United States Patent [19]
Fremy

[11] Patent Number: 6,020,529
[45] Date of Patent: Feb. 1, 2000

[54] SYNTHESIS OF ORGANIC DISULPHIDES AND POLYSULPHIDES

[75] Inventor: Georges Fremy, Os-Marsillon, France

[73] Assignee: Elf Atochem S.A., France

[21] Appl. No.: 09/232,690

[22] Filed: Jan. 19, 1999

[30] Foreign Application Priority Data

Jan. 22, 1998 [FR] France .................................. 98 00660

[51] Int. Cl.⁷ .................................................. C07C 321/12
[52] U.S. Cl. .................................................. 568/21; 568/26
[58] Field of Search .................................. 568/21, 25, 26

[56] References Cited

U.S. PATENT DOCUMENTS 5,068,445 11/1991 Arretz ......................................... 568/21
5,767,229 6/1998 Arretz et al. .
5,786,511 7/1998 Arretz .

FOREIGN PATENT DOCUMENTS 337837 10/1989 European Pat. Off. .
WO 97/21649 6/1997 WIPO .
WO 97/21673 6/1997 WIPO .

OTHER PUBLICATIONS

"Preparation of new weakly–basic anion exchangers", A.V. Pashkov, et al., Chemical Abstracts N. 88:153338h, Plastics Manuf., 1978, p. 23.

*Primary Examiner*—Gary Geist
*Assistant Examiner*—Jean F Vollano

[57] ABSTRACT

A process for the manufacture of organic disulphides and polysulphides using a basic resin catalyst wherein the catalyst is a polystyrene-divinylbenzene resin functionalized with ethylenediamine or a polyethylenepolyamine groups.

11 Claims, No Drawings

SYNTHESIS OF ORGANIC DISULPHIDES AND POLYSULPHIDES

FIELD OF THE INVENTION

The present invention relates to the field of organic disulphides and polysulphides R—$S_n$—R (with $n \geq 2$) and more particularly to their production by reaction of mercaptans with sulphur in the presence of basic resins which act as catalysts, according to the reaction:

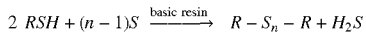

$$2\ RSH + (n-1)S \xrightarrow{\text{basic resin}} R - S_n - R + H_2S$$

BACKGROUND OF THE INVENTION

In the presence of these same basic resins, organic disulphides and polysulphides of low sulphur order can be converted into polysulphides of higher sulphur order by reaction with sulphur. Similarly, in the presence of these same basic resins, organic polysulphides of high sulphur order can be converted into polysulphides of lower sulphur order by reaction with mercaptans.

Thus, patent application EP-A-337,837 teaches the preparation of organic disulphides and polysulphides catalysed by organic anion exchange resins containing tertiary amine or quaternary ammonium functional groups (active in hydroxide form). Such resins, generally in the form of grains or beads which are insoluble in liquid reaction media and are thus easy to separate out at the end of the reaction, allow organic disulphides and polysulphides to be obtained by reaction of elemental sulphur with mercaptans and also allow organic polysulphides of high sulphur order to be obtained by reaction of elemental sulphur with organic polysulphides of lower sulphur order.

According to patent application FR 2,742,144, the use of basic resins containing a primary amine function makes it possible, when compared with resins containing a tertiary amine function, to obtain a better degree of conversion of the reactants and/or a faster rate of reaction.

Similarly, patent application FR 2,742,145 recommends the use of strongly basic resins containing a guanidine or amidine function, which also makes it possible, when compared with resins containing a tertiary amine function, to obtain a better degree of conversion of the reactants and/or a faster reaction rate.

DESCRIPTION OF THE INVENTION

The aim of the present invention is to further improve these results in order to obtain a better degree of conversion of the reactants and/or a faster reaction rate.

This aim is achieved by the use of resins functionalized with ethylenediamine or polyethylene-polyamine groups.

More precisely, the present invention proposes a process for the preparation of organic disulphides and polysulphides by reaction of sulphur with a mercaptan or with a polysulphide of lower sulphur order in order to convert it into polysulphide of higher order, or alternatively by reaction of a mercaptan with an organic polysulphide of high sulphur order in order to convert it into polysulphide of lower sulphur order, in the presence of a catalyst in the form of a resin with basic functions, characterized in that the resin is based on polystyrene-divinylbenzene (PS-DVB) functionalized with ethylenediamine or polyethylenepolyamine groups, it being possible for this resin to be represented by the general formula (I):

EXAMPLES

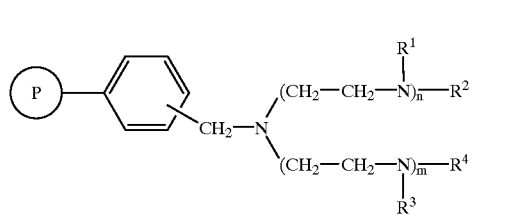

in which:

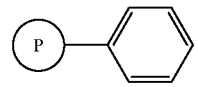

the symbols $R^1$, $R^2$, $R^3$ and $R^4$, which may be identical or different, each represent a hydrogen atom or an alkyl, cycloalkyl, aryl or arylalkyl radical, n is an integer ranging from 1 to 6, m does not exceed n and is equal to 0 or is an integer which can be up to 5.

The resins which serve as starting materials for the preparation of the resins containing an ethylenediamine or polyethylenepolyamine function of general formula (I) can be PS-DVB copolymers or chloromethyl PS-DVB copolymers which, by appropriate chemical reactions described below, are converted into resins containing an ethylenediamine or polyethylene-polyamine function according to the invention.

With a low content of divinylbenzene (0.5 to 7% by weight) as crosslinking agent, copolymers of the gel type are obtained, whereas with higher DVB contents, macro-crosslinked resins of macroporous structure can be obtained. The DVB content can be from 0.5% to 60% by weight relative to the total weight of the PS-DVB copolymer.

Preferably, the starting materials and, consequently, the resins of general formula (I) are macrocrosslinked and of macroporous structure, since these characteristics entail better catalytic activity than is the case with resins of gel type.

These PS-DVB resins can be chloromethylated with chloromethyl ether, according to known techniques which are described in the literature, to variable chlorine contents generally ranging from 1 to 20% by weight of chlorine relative to the weight of chloromethyl resin.

The resins according to the invention can be prepared, according to known amination techniques described in the literature, by reaction of a chloromethyl PS-DVB resin with ethylenediamine or a polyethylenepolyamine of general formula (II):

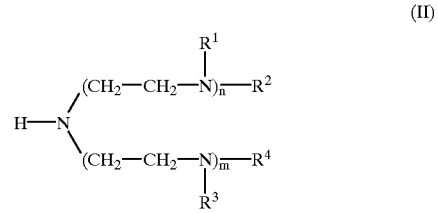

in which the symbols m, n, $R^1$, $R^2$, $R^3$ and $R^4$ have the same meanings as above. In general, the amine (II) in excess is dissolved in a solvent for swelling the chloromethyl resin (for example tetrahydrofuran); the chloromethyl resin is introduced into this solution and the reaction mixture is stirred for a period ranging from a few hours to several days (generally from 4 hours to 4 days) at a temperature which can range from about 20° C. to the boiling point of the solvent, but must not exceed the stability limit temperature of the resin (generally 100° C.). At the end of the reaction, the resin is washed with sodium hydroxide and then with a solvent of low boiling point (for example acetone) in order to help it to dry.

Preferably, an amine of formula (II) is used, in which n is an integer ranging from 1 to 5, m is equal to 0 and the symbols $R^1$, $R^2$ and $R^4$ are hydrogen atoms.

The hydrocarbon radicals R of the organic mercaptans, disulphides and polysulphides are generally alkyl, cycloalkyl, aryl, arylalkyl or alkylaryl groups. These radicals R can bear one or more functional groups such as, for example, halogen atoms and —OH, —OR', —SR', NR'R", —CN, —CHO, —COR' and —COOR' groups, the symbols R' and R" denoting $C_1$ to $C_{12}$ aliphatic radicals or cycloaliphatic, aromatic or alkylaromatic radicals.

The present invention applies in particular to the production of dialkyl disulphides and polysulphides containing from 2 to 40 carbon atoms in total, such as, for example, dimethyl, diethyl, dipropyl, dibutyl, dipentyl, dihexyl, diheptyl, dioctyl, didecyl and didodecyl disulphides and polysulphides. It also applies to the preparation of cycloalkyl disulphides and polysulphides such as, for example, dicyclohexyl disulphide and polysulphides, as well as to the preparation of aromatic disulphides or polysulphides, such as diphenyl disulphide and polysulphides.

The catalytic activity of the resins used in the present invention appears at very low resin contents. Advantageously, the resin is present in an amount ranging from 0.01 to 20 parts by weight per 100 parts by weight of reaction mixture, including resin.

The process according to the invention uses a reaction which may be carried out at a temperature of from –10° C. to 150° C. The temperature is preferably from +10° C. to 120° C.

The reactions may be performed at atmospheric pressure or at higher pressures which may reach 50 bar. In the case of relatively non-volatile reactants of low vapour pressure, the reaction may be performed at pressures below atmospheric pressure, optionally in the presence of an inert gas, such as nitrogen.

The mercaptan/sulphur molar ratio depends on the nature of the mercaptan used and on the product to be prepared (disulphide or polysulphide). Advantageously, this ratio is from 0.3 to 10 and preferably from 0.4 to 6.

When an organic polysulphide of high sulphur order is used at the start in order to convert it into organic polysulphide of low sulphur order, for example into trisulphide R—$S_3$—R or disulphide R—$S_2$—R by the action of the corresponding mercaptan, a mercaptan/polysulphide molar ratio ranging from 2 to 10 is advantageously used.

The production of organic disulphides or polysulphides in the presence of PS-DVB resins containing ethylenediamine or polyethylenepolyamine functions can be carried out in a stirred or tubular reactor, according to a batchwise process, either by loading the reactants before reacting them, or by gradual addition of one of the reactants into the reactor, or alternatively according to a continuous process with controlled addition of the reactants.

In the case where sulphur is one of the reactants (the other being a mercaptan or a polysulphide of low sulphur order), it may be introduced in liquid or solid form.

In addition to the preceding description, the present invention will be better understood with the aid of the experimental section which follows for purely illustrative purposes.

Example 1

Preparation of the Resins According to the Invention

A chloromethyl PS-DVB macroporous resin having the following characteristics was used:

specific surface: 22.5 $m^2$/g of dry resin average pore diameter: 2 nm pore volume: 0.69 ml/g mmol of chlorine/g of resin: 5.4 mmol/g of dry resin 10 g of dry chloromethyl resin (i.e. 54 mmol of chlorine) were weighed out and placed in contact, under a nitrogen atmosphere, with 6.48 g (108 mmol) of ethylenediamine diluted in 130 ml of tetrahydrofuran (THF) predried over molecular sieves. The reaction mixture thus obtained was stirred mechanically for 48 hours at 60° C.

After cooling to 20° C., the resin was filtered off and washed successively with THF, then with 20 ml of aqueous 10% sodium hydroxide solution, next with water until neutral and finally with acetone, before being dried under vacuum at 60° C. to a constant weight.

A PS-DVB resin containing ethylenediamine functions (referred to hereinbelow as EDA resin) containing 7.6% by weight of nitrogen, i.e. 2.70 mmol of ethylenediamine per gram of dry resin, was thus obtained.

Working as above, but replacing the ethylenediamine with an equivalent molar amount of diethylenetriamine (11.2 g), of triethylenetetraamine (15.77 g), of tetraethylenepentaamine (20.41 g) or of penta-ethylenehexaamine (25.06 g), other resins according to the invention, identified as DETA, TETA, TEPA and PEXA respectively, were obtained. Their characteristics are collated in the following table.

The characteristics of PS-DVB resins according to the prior art, namely a resin containing tetramethylguanidine functions (referred to hereinbelow as TMG resin) prepared as above, but replacing the ethylenediamine with 12.5 g of tetramethylguanidine;

a resin containing triazabicyclodecene functions (referred to hereinbelow as TBD resin) prepared as described on pages 23 and 24 of patent application FR 2,742,145, are also given in this table.

| Resin | N % | mmol/g of dry resin |
|-------|------|---------------------|
| EDA   | 7.6  | 2.7 mmol of EDA/g   |
| DETA  | 9.0  | 2.13 mmol of DETA/g |
| TETA  | 10.6 | 1.9 mmol of TETA/g  |
| TEPA  | 11.8 | 1.68 mmol of TEPA/g |
| PEXA  | 11.6 | 1.38 mmol of PEXA/g |
| TMG   | 8.74 | 2.08 mmol of TMG/g  |
| TBD   | 11.29| 2.69 mmol of TBD/g  |

Example 2

Synthesis of di(tert-dodecyl) trisulphide by Reaction of tert-dodecyl Mercaptan with Sulphur in the Presence of Basic Resins Tests for the production of bis(tert-dodecyl) trisulphide were carried out under identical experimental conditions, using the EDA, DETA, TETA, TEPA and PEXA resins according to the invention as catalysts.

Comparative tests were also carried out using the resins of the prior art, namely:

Amberlyst A21 resin from Rohm & Haas, which is a macroporous-type PS-DVB resin containing —CH$_2$N(CH$_3$)$_2$ functions, having a specific surface of 39.8 m$^2$/g and 4.4 mmol of tertiary amine functions/g of dry resin;

Purolite A109 resin, which is a macrocrosslinked PS-DVB resin of macroporous structure containing —CH$_2$NH$_2$ functions (4.3 mmol of NH$_2$/g of dry resin);

the TMG and TBD resins according to patent application FR 2,742,145.

These tests were carried out in apparatus comprising a 250 ml glass jacketed reactor equipped with:

a sinter before the drainage valve, an inlet for introducing nitrogen via a dip tube ending with a sinter (flow rate of nitrogen controlled by a ball flowmeter), a water-cooled condenser connected to the fume cupboard vacuum via a bubble counter containing oil, a thermostatically regulated bath allowing oil to be circulated in the jacket, a glass stirrer ending with a PTFE anchorpaddle and fitted with a stirrer motor with a tachometer, a thermometer probe in a glass sheath.

After the reactor had been placed under a nitrogen atmosphere, 6 g or 15 g of resin (i.e. a catalyst/RSH ratio=4% or 10% respectively) were introduced therein, followed by 151.2 g (750 mmol) of tert-dodecyl mercaptan (TDM). The reactor was then heated to 90° C., after which 24 g (750 mmol) of sulphur were added in a single portion. With the stirring continuing at 500 rev/min, the sulphur dissolved in about 30 minutes.

After switching on the nitrogen bubbling (flow rate=12 l/h) for the entire duration of the reaction, samples were taken over time (t=0 at the time of introduction of the sulphur) in order to determine the residual mercaptan content (% by mass) by argentimetry and the free sulphur content by HPLC; the residual mercaptan content makes it possible to determine the degree of conversion of the TDM.

At the end of the reaction, the polysulphide is filtered while hot (40° C.) through the reactor sinter and the resin is ready to be reused with a fresh load of TDM and sulphur.

The results obtained with the various resins are collated in the following table.

| Test No. | Resin | % catalyst | Conversion of the TDM after reaction for 4 hours (%) |
|---|---|---|---|
| 1 | A-21 | 4 | 65 |
| 2 | " | 10 | 69 |
| 3 | A-109 | 4 | 68 |
| 4 | " | 10 | 73 |
| 5 | TMG | 4 | 74 |
| 6 | TBD | 4 | 73 |
| 7 | EDA | 4 | 80 |
| 8 | " | 10 | 88 |
| 9 | DETA | 4 | 82 |
| 10 | " | 10 | 89 |
| 11 | TETA | 4 | 86 |
| 12 | " | 10 | 90 |
| 13 | TEPA | 4 | 86 |
| 14 | PEXA | 4 | 86 |

Examination of these results shows that the resins containing ethylenediamine or polyethylenepolyamine functions according to the invention (Tests 7 to 14) have higher activity than resins containing tertiary amine functions (Tests 1 and 2), primary amine functions (Tests 3 and 4) or guanidine functions (Tests 5 and 6)

Example3

Synthesis of bis(tert-dodecyl) pentasulphide by Reaction of tert-dodecyl Mercaptan with Sulphur in the Presence of Basic Resins 6 g of resin (i.e. a catalyst/RSH ratio=4%) were introduced into the reactor, placed beforehand under a nitrogen atmosphere, followed by 151.2 g (750 mmol) of TDM, in the same apparatus as in Example 2. After bringing the reactor to 90° C., 48 g (1.5 mol) of sulphur were introduced therein in three portions with intervals of 10 minutes. With the stirring maintained at 500 rev/min, the sulphur dissolved completely in about 45 minutes.

After switching on the nitrogen bubbling (flow rate=6 l/h) for the entire duration of the reaction, the process was then carried out as in Example 2. The test results are collated in the following table.

| Test No. | Resin | Conversion of TDM after: 1 hour | 3 hours |
|---|---|---|---|
| 15 | A-21 | 86% | 97% |
| 16 | TMG | — | 91% |
| 17 | A-109 | — | 95% |
| 18 | DETA | 94% | 99% |

Examination of this table shows that the resin according to the invention (Test 18) gives better results than the resins of the prior art (Tests 15 to 17).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Process comprising preparing organic disulphides and polysulphides R—S$_n$—R (with n≧2) by reacting sulphur with a mercaptan R-SH or with a polysulphide of lower sulphur order to convert it into polysulphide of higher order, or by reacting of a mercaptan with an organic polysulphide of high sulphur order to convert it into polysulphide of lower sulphur order, in the presence of a catalyst in the form of a resin with basic functions, the resin being based on polystyrene-divinylbenzene (PS-DBV) functionalized with ethylenediamine or polyethylenepolyamine groups, this resin having formula (I):

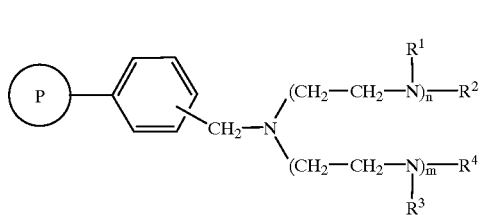

in which:

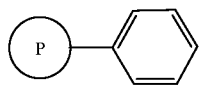

represents the PS-DVB resin support, the symbols $R^1$, $R^2$ $R^3$ and $R^4$, which are identical or different, each represent a hydrogen atom or an alkyl, cycloalkyl, aryl or arylalkyl radical, n is an integer ranging from 1 to 6, m does not exceed n and is equal to 0 or is an integer which can be up to 5.

2. Process according to claim 1, wherein a macro-crosslinked resin of macroporous structure is used.

3. Process according to claim 1, wherein the hydrocarbon radicals R of the organic mercaptans, disulphides and polysulphides are alkyl, cycloalkyl, aryl or arylalkyl groups optionally bearing at least one functional group.

4. Proccess according to claim 1, wherein the resin is present in an amount ranging from 0.01 to 20 parts by weight per 100 parts by weight of reaction mixture, including resin.

5. Process according to claim 1, wherein the reaction is carried out at a temperature of between −10° C. and 150° C.

6. Process according to claim 1 for the preparation of a disulphide or polysulphide comprising starting with a mercaptan and sulphur, the mercaptan/sulphur molar ratio being between 0.3 and 10.

7. Process according to claim 1 for the preparation of a polysulphide of low sulphur order comprising starting with a polysulphide of high sulphur order, the mercaptan/polysulphide molar ratio is between 2 and 10.

8. Process according to claim 1, wherein the functionalized resin results from the reaction of a chloromethylated PS-DVB resin with an excess of ethylenediamine or of a polyethylenepolyamine of formula (II):

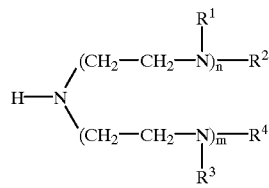

in which the simbols m, n, $R^1$, $R^2$, $R^3$ and $R^4$ have the same meanings as in claim 1.

9. Process according to claim 8, wherein n is an integer ranging from 1 to 5, m is equal to 0 and the symbols $R^1$, $R^2$ and $R^4$ are hydrogen atoms.

10. Process according to claim 5, wherein the temperature is between +10° C. and 120° C.

11. Process according to claim 6, wherein the molar ratio is between 0.4 and 6.

* * * * *